United States Patent [19]
Kletecka et al.

[11] Patent Number: 5,026,849
[45] Date of Patent: Jun. 25, 1991

[54] SOLVENTLESS PROCESS FOR PREPARING A TRI-SUBSTITUTED TRIAZINE

[75] Inventors: George Kletecka, Fairview Park; Victor L. Ledesma, Avon Lake, both of Ohio

[73] Assignee: The B. F. Goodrich Company, Akron, Ohio

[21] Appl. No.: 364,342

[22] Filed: Jun. 9, 1989

[51] Int. Cl.$^5$ .................. C07D 401/12; C07D 403/12
[52] U.S. Cl. .................................... 544/198; 544/212; 544/207; 544/209
[58] Field of Search ................ 544/212, 198, 207, 209

[56] References Cited

U.S. PATENT DOCUMENTS

| | | | |
|---|---|---|---|
| 4,480,092 | 10/1984 | Lai et al. | 544/113 |
| 4,629,752 | 12/1986 | Lai et al. | 544/113 |
| 4,731,393 | 3/1988 | Karrer et al. | 522/117 |

Primary Examiner—John M. Ford
Attorney, Agent, or Firm—Alfred D. Lobo

[57] ABSTRACT

A process is taught for recovering a white reaction product of a cyanuric halide with an amine reactant (white being indicative of the product's high purity), in high yield. In the absence of a solvent for either reactant, the first step comprises reacting the cyanuric halide, as a finely divided solid, with a liquid amine which is to provide a saturated heterocyclic amine group, such as a polysubstituted piperazinone, piperazine, or piperidine as the substituent for each of the three halogen atoms of the cyanuric halide used. This solventless process carried out under essentially anhydrous conditions, with a large molar excess of the amine reactant chosen, not only shortens the long time required to make the desired tri-substitution in a conventional solvent process, but also obviates using a pressurized reactor. Since (i) the reaction temperature is relatively low, (ii) there is no solvent, and (iii) the amine reactants are relatively high-boiling, and the reaction occurs in the liquid phase, there is no build-up of pressure. Fortuitously, the appropriate amount of alkanol and concentrated aqueous alkali provides a partition coefficient such that salt formed by neutralization of the excess amine hydrohalide is effectively precipitated nearly quantitatively. In addition to providing "easy" processing conditions, the solventless reaction in our process provides higher yields than can be obtained, under comparable conditions, with the 'solvent process'; a lower by-product 'make' because of the low temperature and substantially atmospheric pressure used; and, the batch reaction is completed in less than 12 hr.

15 Claims, 1 Drawing Sheet

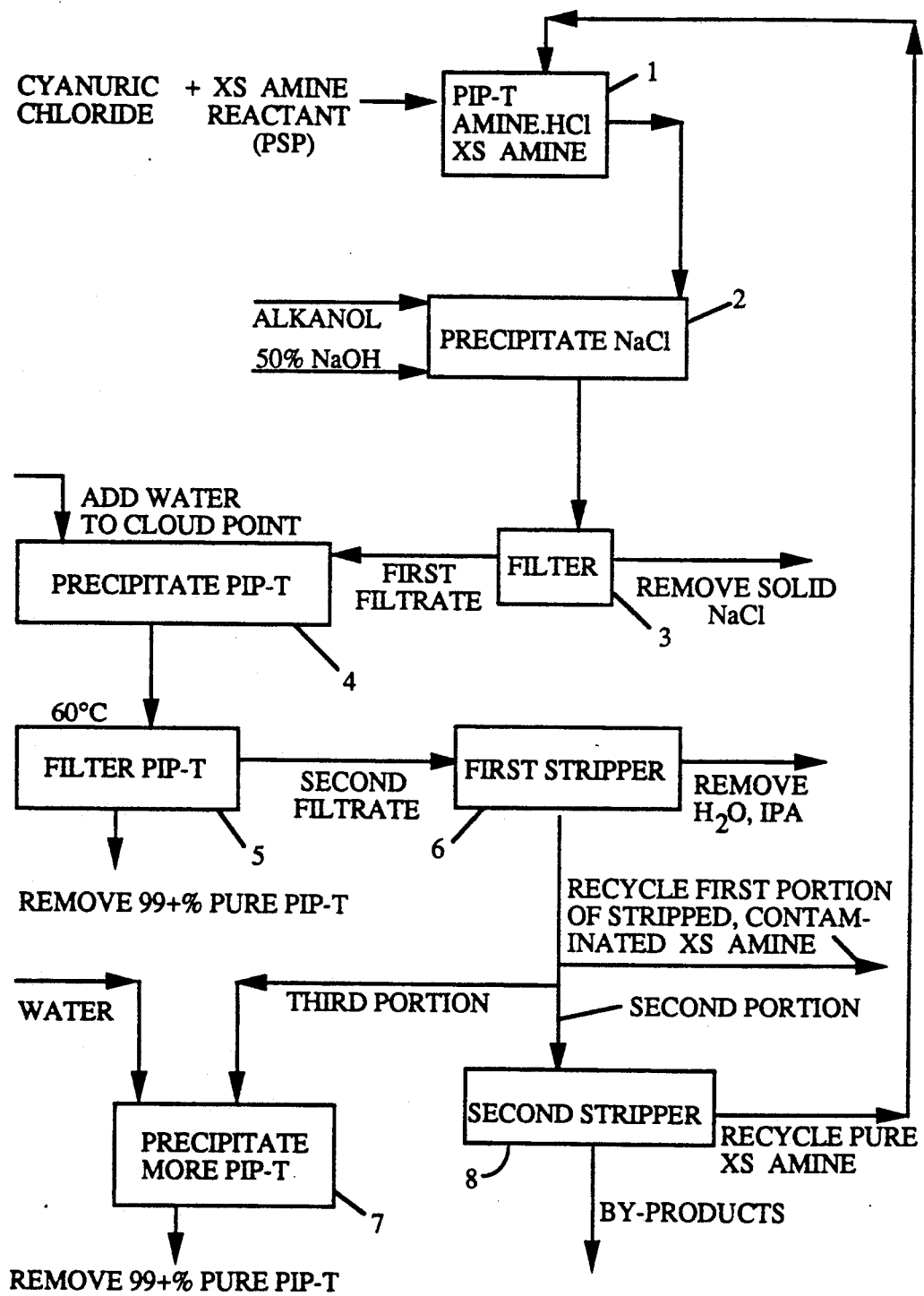

SOLVENTLESS PROCESS FOR PREPARING A TRI-SUBSTITUTED TRIAZINE

BACKGROUND OF THE INVENTION

This invention relates generally to a process for recovering a white reaction product of a cyanuric halide with an amine reactant (white being indicative of the product's high purity), in high yield. The first step of the process comprises reacting the cyanuric halide as a finely divided solid with a liquid amine in which the solid is not soluble up to about 50° C. In such a situation, it is conventional to provide a common solvent for the solid and the amine, or at least for one or the other, with the expectation that the solvent will provide the medium in which the reaction may proceed with less restraint than if no solvent was present. Particularly in an industrial environment where a large quantity of product is to be made, it is essential to ensure that the reaction proceeds controllably, and in as little time as is safely practical. These considerations dictate that the choice of an appropriate solvent be the primary consideration in the first step of the process, which was done in the prior art process referred to herein as the "solvent process".

Even if the function of the solvent chosen for the amine was only to disperse the solid cyanuric halide thoroughly in the reaction mass, so that clumping of the solid is avoided, the solvent for the amine discharged a dual function. The solvent maximized the availability of the reactive halogen atoms, and it allowed the reaction to proceed controllably. The substitution of the three halogen atoms on the triazine ring, proceeds in the process of this invention, without a solvent.

More specifically, this invention relates to a process for producing a high purity (at least 97% pure) tri-substituted triazine, the first step of which process comprises substituting each of three chlorine (or other halogen) atoms on a trihalo-s-triazine, specifically cyanuric chloride, with a polysubstituted piperazinone, polysubstituted piperazine, or polysubstituted piperidine ("PSP" for brevity), so as to form a substituted triazine with a PSP substituent at each of the 2, 4 and 6 positions. The substituted triazine is represented by the structure

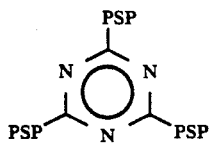

wherein PSP represents a substituent selected from the group consisting of structures (A)

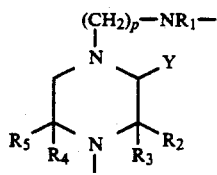

and

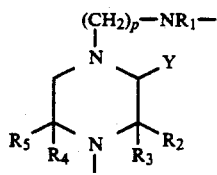

wherein,

Y represents H or =O, $R_1$ represents $C_1$-$C_{24}$ alkyl, $C_5$-$C_7$ cycloalkyl, $C_7$-$C_{20}$ aralkyl, $C_1$-$C_{24}$ aminoalkyl, and $C_6$-$C_{20}$ aminocycloalkyl;

$R_2$, $R_3$, $R_4$, and $R_5$ independently represent $C_1$-$C_{24}$ alkyl;

$R_6$, and $R_7$ independently represent $C_1$-$C_{24}$ alkyl and polymethylene having from 4 to 7 C atoms which are cyclizable; and, p represents an integer in the range from 2 to about 10;

$R_8$ represents H, $C_1$-$C_6$ alkyl and phenyl; and, (B)

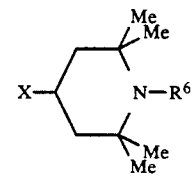

wherein Me=methyl, $R^6$ represents hydrogen, oxyl oxygen, $C_1$-$C_{12}$-alkyl, $C_3$-$C_7$-alkenyl, $C_7$-$C_{11}$-phenylalkyl, cyanomethyl, $C_2$-$C_{18}$-alkanoyl, or $C_3$-$C_{18}$-alkenoyl, or a group —CON($R^7$)($R^8$) in which $R^7$ is $C_1$-$C_{12}$-alkyl, allyl, cyclohexyl, benzyl, phenyl, or $C_7$-$C_{12}$-alkylphenyl, and $R^8$ is hydrogen, $C_1$-$C_{12}$-alkyl, allyl or benzyl or $R^7$ or $R^8$ together with the N atom to which they are attached, form a 5-membered ring or 6-membered heterocyclic ring; and, X is a divalent group of the formula —O—, —NH—$CH_2$—$CH_2$—, —NH—($CH_2$)$_2$—O— and the like.

Such triazines substituted with a polysubstituted piperazinone are referred to in U.S. Pat. Nos. 4,480,092 and 4,692,752 as "PIP-Ts" (acronym for piperazinone-triazine) which are disclosed as being stabilizers for organic compounds. Other triazines tri-substituted with a polysubstituted piperidine are referred to in U.S. Pat. No. 4,731,393, the disclosure of which is incorporated by reference thereto as if fully set forth herein. All tri-substituted triazines are referred to herein as PIP-Ts irrespective of the PSP substituents.

The PIP-T tri-substituted with polysubstituted piperazinones, and precursor mono- and di-substituted PIP-Ts, were prepared by dispersing finely divided solid cyanuric halide such as cyanuric chloride in an aromatic solvent such as toluene, or an aliphatic solvent such as hexane, and reacting the cyanuric chloride with the PSP amine reactant (hereafter "amine reactant" for brevity) from which the PSP substitutent is to be derived. Typically, the amine reactant was dissolved in toluene or an aliphatic solvent such as hexane, and the reaction carried out at elevated temperature with the addition of dilute aqueous alkali. NH4OH or an alkali metal hydroxide, say NaOH, are used to neutralize the hydrogen halide, such as HCl generated during the reaction of cyanuric chloride with the amine reactant. The alkali was used to neutralize the HCl generated during the reaction, before the HCl could react with the amine reactant present. The prior art reaction was not carried out under essentially anhydrous conditions.

This laboratory process was subsequently scaled up for commercial production of PIP-Ts, except that, to obtain a commercially acceptable yield of product in a reasonable period of time, say 14 hr, it became necessary to use a larger excess of amine reactant, still requiring a large amount of solvent; and, it became necessary to carry out the reaction at a temperature in excess of 175° C. at a pressure in excess of 150 psig. Under carefully controlled conditions, the yield of acceptable PIP-T product was typically no more than 80%; the quality of the desired PIP-T product was vitiated; undesirable by-products were formed; and, the excess amine reactant was not economically recoverable. The recovery of at least 80%, and preferably more than 90%, of the excess amine reactant used in the first step of the process, is critical to the commercial success of the process because, typically, the cost of the amine reactant is many times greater than that of cyanuric halide, all of which cyanuric halide must be converted to the tri-substituted triazine product if it is to be substantially the only cyanuric halide/amine reactant reaction product to be recovered.

The tri-substitution of the halogens on a cyanuric halide with polysubstituted piperidines was conventionally done in toluene as solvent, and at low temperature, with the result that the reaction is too slow to be commercially feasible.

The process of this invention provides a solventless reaction mass in which the desired reaction (the first step of this process) proceeds at relatively high speed, at practical low temperature and pressure under essentially anhydrous conditions. In a subsequent step, the deliberate addition of an appropriate preselected amount of a lower $C_1$-$C_6$ branched or straight chain alkanol, first to thin the thick solution which typically results after the reaction is complete, and then the addition of aqueous alkali to form the salt, was found unexpectedly to precipitate salt, usually NH4Cl or NaCl, from solution in a mixture of three liquids, namely: unreacted excess (XS) amine reactant, alkanol and a relatively very small amount of water, in which mixture the PIP-T product is dissolved. In still another subsequent step, the deliberate addition of more water to the NaCl-free mixture of alkanol, and XS amine reactant produced more product, as it was discovered that this procedure precipitated the desired PIP-T product in essentially pure form.

The key to the effectiveness of the process is the forced solubility of solid cyanuric halide in the amine reactant with immediate subsequent displacement of a first halogen atom. Displacement of the first halide atom might be expected to occur relatively easily, that is, at relatively low temperature, and it does.

But the second halogen atom is not as easily displaced as was the first, and it is even more difficult to displace also the third. In the absence of a solvent, at the elevated temperature one would expect to use to trisubstitute the triazine ring, it was not evident that the halogen atoms would be displaced by only the H atom on the terminal N atom of the PSP, to the exclusion of the H atom on the $N^4$ atom of the piperazinone ring. Still further, since it was evident that, irrespective of which H atom displaced the Cl, Br, or F atoms on the triazine ring, the HCl, HBr or HF formed would react with the amine reactant making it unavailable for reaction with the cyanuric halide, carrying out the reaction in the absence of an alkali, seemed ingenuous.

Moreover, because there was no readily adaptable process to recover the XS amine reactant from the hydrochloride (say) of the XS amine reactant, not to mention removing the salt formed, the solventless reaction of the first step seemed misdirected. Recovering and recycling the XS amine reactant is an essential factor of the process because of the high cost of the amine reactant. Yet, because this solventless reaction proceeds relatively rapidly (less than 12 hr) with more than 80% yield of product under less than 5 atm pressure, and preferably at substantially atmospheric pressure, it spurred the exploration of techniques to overcome the problems generated by the first step. It is this exploration which opened the door to the solutions embodied in the several subsequent steps which together provide a highly effective process for making the product.

SUMMARY OF THE INVENTION

It has been discovered that the long time required to substitute each of three halogens on cyanuric halide with a substituent having a saturated heterocyclic amine group, such as a polysubstituted piperazinone, piperazine, or piperidine (each referred to as "PSP" for brevity), can not only be shortened, but the reaction can be run at ambient pressure because, without a solvent, the relatively high-boiling PSP amine reactants do not elevate the ambient pressure at the temperature of the reaction if no solvent for either reactant is used, thus making it possible to carry out the reaction economically.

In the tri-substitution of each of three halogens with a polysubstituted piperazin-2-one, it has been discovered that the relatively high temperature and pressure used in a commercial prior art solvent process in which a reaction of cyanuric halide with a PSP amine reactant was carried out over more than 12 hr, can be avoided if the reaction is carried out in the absence of a solvent for either reactant. A solventless reaction with the same amount of cyanuric halide as in the 'solvent process' provides higher yield and a lower by-product 'make', at low temperature and substantially atmospheric pressure, in less than 12 hr.

It has more specifically been discovered that the first step of a process for preparing a tri-substituted cyanuric halide (PIP-T) of exceptionally high purity and yield, comprises reacting finely divided solid cyanuric halide, and, an amine reactant having a boiling point in excess of 200° C., at near-atmospheric pressure under essentially anhydrous conditions at relatively low temperature, in a solventless reaction mass, provided that the amine reactant is present in a very large excess.

It is therefore a general object of this invention to provide a process for producing a PIP-T about 97+% pure, in an yield in excess of 80%, in a reaction zone operating at a pressure and temperature lower than that used in the prior art solvent process. After the reaction is complete, the reaction mass is diluted with cold alkanol, say isopropyl alcohol (IPA), and the hydrohalide of the amine reactant formed during the reaction is neutralized with relatively concentrated aqueous alkali so as to precipitate substantially all the salt formed, e.g. NH₄Cl or NaCl, as solid which is filtered; essentially salt-free filtrate, comprising the PIP-T, excess amine reactant, alkanol and water is deliberately diluted with enough water to precipitate solid PIP-T product which is filtered. The filtrate, containing by-products of the reaction, excess amine reactant, alkanol and water, is stripped to recover first the alkanol and water, and further stripped, preferably under reduced pressure, to recover the excess amine reactant. The remaining tarry residue is disposed of.

It is a specific object of this invention to provide a process in which a combination of an alkanol and the appropriate amount of water provides a partition coefficient for the salt (formed upon neutralization of amine hydrochloride) such that more than 95% of the solid salt precipitates and can be separated from the liquid by a conventional solid-liquid separation unit operation such as by filtration.

It is still another specific object of this invention to provide a process in which an essentially salt-free solution of PIP-T in excess amine reactant, alkanol and water may precipitate the PIP-T from the solution in solid form, if sufficient additional water is added to reach the cloud point of the solution, so that the solid PIP-T may be separated from the liquid by a conventional solid-liquid separation unit operation such as by filtration.

It is yet another specific object of this invention to provide a process in which additional amounts of essentially pure and white PIP-T, namely amounts in addition to that separated in the solid-liquid separation step referred to hereinabove, may be separated by repeated additions of water to precipitate the additional amounts of PIP-T, so that in excess of 90% of the theoretical yield of PIP-T may be recovered, and in excess of 90% of the unreacted amine reactant may also be recovered and recycled to the solventless reaction zone.

BRIEF DESCRIPTION OF THE DRAWING

The foregoing and other objects and advantages of our invention will appear more fully from the following detailed description, made in connection with the accompanying flowsheet of the process schematically illustrating the various steps of the process of this invention.

DETAILED DESCRIPTION OF A PREFERRED EMBODIMENT

The essential steps of the preferred process include, (1) reacting in a solventless reaction zone, under essentially anhydrous conditions, solid, finely divided particles of cyanuric halide with a PSP amine reactant present in a molar excess in the range from 2 to 10 times the amount required to displace each of the halogen atoms of the cyanuric halide, in the absence of a solvent for either reactant, at a temperature in the range from about 100° C. to about 150° C., and substantially atmospheric pressure;

(2) adding a lower alkanol and a relatively concentrated aqueous base, the amount of the latter being sufficient to neutralize the hydrohalide of the PSP amine reactant (PSP.HQ, for brevity, wherein Q represents halogen) formed by reaction of HQ, generated during the reaction, with excess amine reactant, but the amount of water being less than will precipitate PIP-T from solution; the amount of the alkanol, in combination with the water present, being sufficient to precipitate at least 90% of all salt formed upon neutralization of the PSP.HQ, as solid;

(3) separating solid salt from a solution of PIP-T in a first mixture of lower alkanol, water, and excess (XS) amine, which first mixture is recovered as a first filtrate;

(4) adding a sufficient amount of water to the first filtrate to reach the cloud point, and precipitating solid particles of white PIP-T from a second mixture of excess amine reactant, alkanol and water;

(5) separating solid PIP-T which is at least 97% pure, from the second mixture of excess amine reactant, alkanol and water which second mixture is recovered as a second filtrate;

(6) stripping the alkanol and water from the second filtrate and recovering stripped, excess amine reactant contaminated with tarry by-products; and, (7) recycling the excess amine reactant to the solventless reaction zone.

The preparation of a particular PIP-T formed by the reaction of cyanuric chloride with 4-N-butylamino-2,2,6,6-tetramethylpiperidine is represented by the structure:

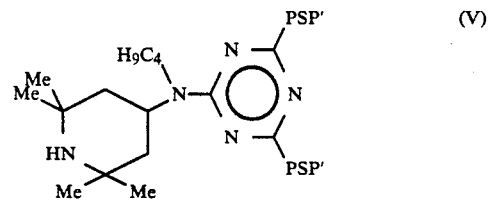

wherein PSP' represents the same structure written for the other substitutent.

Other crystallizable triazines which are tri-substituted with polysubstituted piperidyl substitutents are prepared with 4-N-methylamino-2,2,6,6-tetramethylpiperidine;
4-N-ethylamino-2,2,6,6-tetramethylpiperidine;
4-N-propylamino-2,2,6,6-tetramethylpiperidine;
4-N-isopropylamino-2,2,6,6-tetramethylpiperidine; and,
4-N-isobutylamino-2,2,6,6-tetramethylpiperidine; etc.

Referring to the Figure, there is shown a flowsheet for the preparation of a particular PIP-T formed by the reaction of cyanuric chloride with a particular PSP amine reactant, 1-[3-(cyclohexylamino)propyl]-3,3,5,5-tetramethylpiperazin-2-one, familiarly referred to as cyclohexylpiperazinone, and for brevity, as "CHP", represented by the structure:

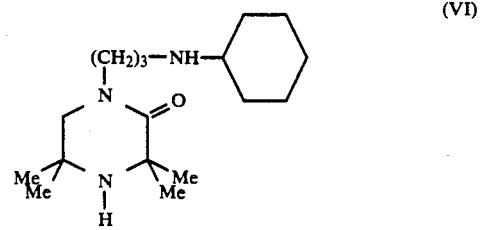

As indicated in the flowsheet, the XS PSP amine reactant is used in large molar excess.

The structure of the desired PIP-T product is represented as follows:

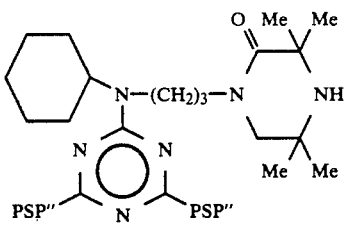

wherein PSP" represents the same structure written for the other substitutent.

Other crystallizable triazines which are tri-substituted with polysubstituted piperazin-2-one substitutents are prepared with 1-[3-(isopropylamino)propyl]-3,3,5,5-tetramethylpiperazin-2-one;
1-[2-(isopropylamino)ethyl]-3,3,5,5-tetramethylpiperazin-2-one;
1-[2-(butylamino)ethyl]-3,3,5,5-tetramethylpiperazin-2-one; and,
1-[2-(cyclohexylamino)ethyl]-3,3,5,5-tetramethylpiperazin-2-one; inter alia.

Still other crystallizable triazines which are tri-substituted with polysubstituted piperazine substitutents are prepared with 1-[3-(isopropylamino)propyl]-3,3,5,5-tetramethylpiperazine;
1-[2-(isopropylamino)ethyl]-3,3,5,5-tetramethylpiperazine;
1-[2-(butylamino)ethyl]-3,3,5,5-tetramethylpiperazine; and,
1-[2-(cyclohexylamino)ethyl]-3,3,5,5-tetramethylpiperazine.

In the flowsheet, there is shown the first step of the process, which step comprises carrying out the reaction under substantially atmospheric pressure at from about 100° C. to 150° C., depending upon the particular PSP amine reactant to be introduced into the triazine ring, and completing the reaction in less than 12 hr, in a reaction zone indicated by reference numeral 1. The reaction is complete when it is determined, by LC analysis (say) made periodically, that all the cyanuric halide is tri-substituted. The hydrohalide HQ generated by displacement of the halogen atoms reacts with excess PSP amine reactant, forming the hydrohalide PSP.HQ; and, the PIP-T formed is dissolved in the hot solventless liquid mass obtained after the reaction is completed. In the flowsheet, the reactor is shown to contain the product PIP-T formed, the PSP amine-HCl (CHP.HCl, in this specific case), and excess PSP amine reactant.

The hot solventless liquid reaction mass is cooled to a temperature below the boiling point of the alkanol to be used, so that flashing alkanol (normally at room temperature) is avoided when it is added to dilute the reaction mass. Typically the reaction mass is cooled in the range from about 10° C. to about 80° C., when a $C_1$-$C_3$ alkanol is used.

The alkanol-diluted reaction mass may be further cooled by addition of cold alkanol. The total amount of alkanol added is sufficient to provide two functions, namely to lower the viscosity of the generally viscous reaction mass, and to provide the appropriate partition coefficient so that, upon neutralization of the hydrohalide of the PSP amine reactant with aqueous alkali, the salt will be precipitated essentially quantitatively. Generally the amount of alkanol added is in the range from 0.5 to 2 times the amount by weight of the PSP amine reactant used in the reaction, and more preferably about an equal amount.

Neutralization is effected with cold concentrated aqueous alkali, preferably aqueous alkali metal hydroxide, until essentially all the salt in the liquid mass is precipitated as solid crystals, in a precipitation zone indicated by reference numeral 2. It is preferred that the aqueous alkali be as concentrated as is practical, so long as it is still in the liquid state, for example 50% NaOH solution. The salt crystals are then filtered in a filtration zone 3, leaving a first filtrate in which the product PIP-T is dissolved. This first filtrate is a mixture of alkanol, the little water introduced with the aqueous alkali, and excess PSP amine reactant, the proportions of each being such that the PIP-T is held in solution. The solid salt crystals are removed from the filter.

Thereafter, if enough additional water is added to this first filtrate at the appropriate temperature so as to reach the cloud point, about 60° C. in this specific case, the PIP-T commences to precipitate from solution, and more than 80% of all the PIP-T will be precipitated in zone 4.

The precipitated PIP-T is filtered in a filtration zone 5, from which flows a second filtrate in which a very small amount of PIP-T, in the range from 5% to 15% of the PIP-T formed in reaction zone 1, may remain in solution, along with comparably small or even smaller quantities of by-products, in the range from 0.5% to about 5% by weight of the PIP-T formed, which by-products would not be acceptable if left in the PIP-T product, particularly if they contribute to coloring the PIP-T product.

The alkanol and water are stripped from the second filtrate in a first stripper in a first stripping zone 6, at a temperature sufficient to strip the lowest boiling azeotrope of water and the alkanol used, this temperature typically being below 100° C., for example in the range from about 70° C. to about 90° C. if isopropanol (IPA) is used, it being recognized that this temperature may be as high as 150° C. when higher boiling alkanols are used. Stripping is conveniently accomplished in a flash drum, but is more effectively done in a conventional fractionation column (stripper) from which flows a stripped, contaminated XS amine bottoms stream, referred to as a "PSP amine-rich stream" because it consists essentially of the excess PSP amine reactant and no more than about 10% by weight of assorted contaminant by-products; the PSP amine-rich stream also contains less than 5%, and typically an even smaller amount of the PIP-T produced in zone 1, which even smaller amount is still unrecovered.

This PSP amine-rich stream, or a first portion thereof, may be recycled to zone 1, as shown, as long as the level of contaminants being introduced into zone 1 remains at an acceptably low level insufficient to affect the melt color of the final PIP-T product adversely. A Garnder melt color above 5 is generally unacceptable in finished PIP-T.

As an alternative, if an essentially pure excess PSP amine stream is to be recycled to zone 1, the entire PSP amine-rich stream (bottoms from the first stripper) may again be stripped in a second stripping zone 8, preferably in a stripper operating at reduced pressure in the range from about 1 mm to about 5 mm Hg, and a temperature below that at which the stability of the amine is deleteriously affected, typically less than 200° C., preferably in the range from 100° C. to about 150° C., to remove an essentially pure PSP amine reactant stream overhead. As shown, this essentially pure excess PSP amine reactant is recycled to the solventless reaction zone 1. The bottoms product from the second stripping zone may be treated further to recover a very small quantity of PIP-T, less than 1%, which might still remain, and also the remaining PSP amine reactant, before the undesired by-products are disposed of.

As another alternative, in addition to recycling a first portion of the stripped, contaminated PSP amine-rich stream, a second portion may be stripped in stripping zone 2, as described immediately hereinabove, and the essentially pure PSP amine reactant recovered as overhead from the second stripper, is recycled to the reaction zone 1.

In another embodiment, if the make of by-products is sufficiently low, the second stripper may not be operated, so that in addition to recycling a first portion of the stripped, contaminated PSP amine-rich stream to the reaction zone 1, a third portion of the bottoms from the first stripper may be further diluted with water to precipitate some or substantially all of the still unrecovered PIP-T in it, which PIP-T, upon being precipitated in zone 7, may be recovered.

In yet another embodiment, in the more typical case where it is essential to operate the second stripper because of the unacceptably high level of by-products made, the bottoms from the first stripper is split into three portions. In addition to recycling a first portion of the stripped, contaminated PSP amine-rich stream; and withdrawing a second portion to be stripped in stripping zone 2, and recycling the overhead from the second stripper; a third portion of the bottoms from the first stripper is withdrawn and further diluted with water, as described hereinabove, to precipitate some or substantially all of the still unrecovered PIP-T in it, which PIP-T, upon being precipitated in zone 7, may be recovered.

In an analogous manner, a triazine ring may be substituted with any substituted monoaza- or diaza- cycloalkane or cycloalkanone having the structures written hereabove, provided, upon neutralization with concentrated aqueous alkali, the salt formed is crystallizable from a mixture of alkanol, water and the excess amine reactant which remains unreacted.

The following illustrative example provides data for the foregoing process to prepare the compound (VII) on a large scale, using cyanuric chloride, IPA as the alkanol, and 50% aqueous NaOH as the aqueous alkali.

EXAMPLE

Preparation of the PIP-T represented by structure VII: 16 moles of the PSP amine reactant represented by structure III are heated to 130° C. in a jacketed glass-lined reactor equipped with a variable speed stirrer and means to introduce nitrogen, to provide a nitrogen blanket. The temperature of the contents of the reactor may be controlled by circulating fluid in the jacket, and the reactor is provided with conventional temperature control means, and a continuous temperature recorder. Also provided is a solids feeder to introduce 1 mole of solid cyanuric chloride gradually while the PSP amine reactant VI is being stirred, maintaining the 130° C. temperature.

A sample of the reaction mass is taken intermittently and analyzed with LC analysis. The reaction is discontinued when there is no trace of the disubstituted PSP. The contents of the reactor are cooled to 90° C. and about 10 moles of cold isopropanol are added to lower the temperature to 60° C. Then 3.15 moles of 50% aqueous NaOH (about a 5% excess over stoichiometric) is added gradually so as to maintain the 60° C. neutralization temperature. NaCl precipitates from solution and the solid NaCl crystals are removed in filtration zone 3 by a first filtration step.

Hot water is added to the first filtrate obtained, to maintain the temperature at about 60° C., until the cloud point is reached. White crystals of PIP-T, having a purity in the range from about 98% to 99% or higher, precipitate in zone 4, and are removed by a second filtration step in filtration zone 5. Nearly one mole of PIP-T product VII is obtained for each mole of cyanuric chloride charged, the yield being in excess of 90%.

The second filtrate obtained is stripped in a first conventional fractionation column in zone 6 to remove water and IPA overhead. The bottoms from the first stripper contains a small quantity of unidentified compounds which are contaminants, and which do not seriously interfere with the reaction of the cyanuric chloride. If the starting materials are sufficiently pure, this bottoms stream may be recycled to the reactor.

After the level of contaminants in the bottoms from the first stripper in zone 6 is more heavily contaminated, a first portion of the bottoms from the first stripper may still be recycled, if desired, but a second and much larger portion is led to a second fractination column in which essentially pure CHP (VI) is removed overhead and recycled to the reactor.

To recover an even greater amount of the CHP, in addition to the foregoing two steps, a third portion of the bottoms from the first stripper is withdrawn and diluted with enough water to reach the cloud point of the solution, and precipitate the desired product VII in substantially pure form.

Having thus provided a general discussion of the problems addressed and solved in our invention, and a specific illustration of the best mode of carrying out the process for a specific PIP-T product desired, it is to be understood that no undue restrictions are to be imposed by reason thereof except as provided by the following claims.

We claim:

1. A process for preparing a tri-substituted triazine having a heterocyclic amine group in the substituent derived from a polysubstituted piperidine, polysubstituted piperazine, or polysubstituted piperazin-2-one, each referred to as a PSP amine reactant, said process comprising,
(a) reacting, in a solventless reaction zone, solid, finely divided particles of cyanuric halide with a PSP amine reactant, present in a molar excess in the range from 2 to 10 times the amount required to displace each of the halogen atoms of the cyanuric halide, in the absence of a solvent for either reactant, at a temperature and pressure sufficient to complete tri-substitution in less than 12 hr;
(b) adding a lower $C_1$–$C_6$-alkanol and a relatively concentrated aqueous solution of an aqueous alkali, the amount of the latter being sufficient to neutralize the hydrohalide of the PSP amine reactant which is formed by reaction of hydrohalide generated during the reaction, with excess amine reactant, but the amount of water being less than will precipitate PIP-T from solution; the amount of the alkanol, in combination with the water present, being sufficient to precipitate at least 90% of all salt formed upon neutralization, as solid;

(c) separating solid salt from a solution of PIP-T in a first mixture of said lower alkanol, water, excess amine reactant, and the hydrohalide of said amine reactant, which first mixture is recovered as a first filtrate;

(d) adding a sufficient amount of water to the first filtrate to reach the cloud point, and precipitating solid particles of white PIP-T from a second mixture of excess amine reactant, alkanol and water;

(e) separating solid PIP-T which is at least 97% pure, from the second mixture of excess amine reactant, alkanol and water which second mixture is recovered as a second filtrate;

(f) stripping the alkanol and water from said second filtrate in a first stripping zone; and, (g) recovering stripped, excess amine reactant contaminated with by-products.

2. The process of claim 1 wherein said tri-substituted triazine is represented by the structure

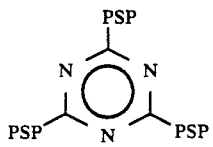

(I)

wherein PSP represents a substituent selected from the group consisting of structures (A)

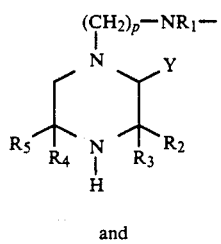

(II)

and

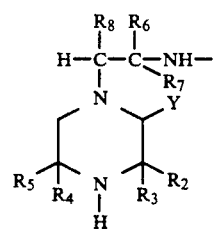

(III)

wherein,

Y represents H or =O, $R_1$ represents $C_1$–$C_{24}$ alkyl, $C_5$–$C_7$ cycloalkyl, $C_7$–$C_{20}$ aralkyl, $C_1$–$C_{24}$ aminoalkyl, and $C_6$–$C_{20}$ aminocycloalkyl;

$R_2$, $R_3$, $R_4$, and $R_5$ independently represent $C_1$–$C_{24}$ alkyl;

$R_6$, and $R_7$ independently represent $C_1$–$C_{24}$ alkyl and polymethylene having from 4 to 7 C atoms which are cyclizable; and, p represents an integer in the range from 2 to about 10;

$R_8$ represents H, $C_1$–$C_6$ alkyl and phenyl; and,

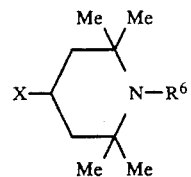

wherein

Me = methyl, $R^6$ represents hydrogen, oxyl oxygen, $C_1$–$C_{12}$-alkyl, $C_3$–$C_7$-alkenyl, $C_7$–$C_{11}$-phenylalkyl, cyanomethyl, $C_2$–$C_{18}$-alkanoyl, or $C_3$–$C_{18}$-alkenoyl, or a group —CON($R^7$)($R^8$) in which $R^7$ is $C_1$–$C_{12}$-alkyl, allyl, cyclohexyl, benzyl, phenyl, or $C_7$–$C_{12}$-alkylphenyl, and $R^8$ is hydrogen, $C_1$–$C_{12}$-alkyl, allyl or benzyl or $R^7$ or $R^8$ together with the N atom to which they are attached, form a 5-membered ring or 6-membered heterocyclic ring; and, X is a divalent group of the formula —O—, —NH—CH$_2$—CH$_2$— and —NH—(CH$_2$)$_2$—O—.

3. The process of claim 2 comprising, recycling from none to all of said stripped, excess amine reactant as a first portion which is returned to said solventless reaction zone.

4. The process of claim 3 comprising, recycling none of said stripped, excess amine reactant, and flowing all of it to a second stripping zone, removing essentially pure excess amine reactant overhead, and recycling said essentially pure excess amine to said solventless reaction zone.

5. The process of claim 3 including, recycling a minor portion of said stripped, excess amine reactant to said reaction zone, and flowing a major portion as a second portion, to a second stripping zone, removing essentially pure excess amine reactant overhead, and recycling said essentially pure excess amine to said solventless reaction zone.

6. The process of claim 4 comprising, in addition, removing a third portion of said stripped, excess amine reactant, diluting it with enough water at a temperature sufficient to reach the cloud point, and precipitating additional tri-substituted triazine product having a purity of at least 97%.

7. The process of claim 5 comprising, in addition, removing a third portion of said stripped, excess amine reactant, diluting it with enough water at a temperature sufficient to reach the cloud point, and precipitating additional tri-substituted triazine product having a purity of at least 97%.

8. The process of claim 2 wherein, said polysubstituted piperidine is selected from the group consisting of 4-N-methylamino-2,2,6,6-tetramethylpiperidine;
4-N-ethylamino-2,2,6,6-tetramethylpiperidine;
4-N-propylamino-2,2,6,6-tetramethylpiperidine;
4-N-isopropylamino-2,2,6,6-tetramethylpiperidine; and,
4-N-isobutylamino-2,2,6,6-tetramethylpiperidine; said polysubstituted piperazine is selected from the group consisting of 1-[3-(isopropylamino)propyl]-3,3,5,5-tetramethylpiperazine;
1-[2-(isopropylamino)ethyl]-3,3,5,5-tetramethylpiperazine;
1-[2-(butylamino)ethyl]-3,3,5,5-tetramethylpiperazine; and, 1-[2-(cyclohexylamino)ethyl]-3,3,5,5-tetramethylpiperazine; said polysubstituted piperazin-2-one is selected from the group consisting of 1-[3-(isopropylamino)propyl]-3,3,5,5-tetramethylpiperazin-2-one;

1-[2-(isopropylamino)ethyl]-3,3,5,5-tetramethylpiperazin-2-one;

1-[2-(butylamino)ethyl]-3,3,5,5-tetramethylpiperazin-2-one; and,

1-[2-(cyclohexylamino)ethyl]-3,3,5,5-tetramethylpiperazin-2-one

9. The process of claim 8 wherein said cyanuric halide is cyanuric chloride, and said alkali is selected from the group consisting of ammonium hydroxide and an alkali metal hydroxide.

10. The process of claim 9 wherein said temperature is in the range from about 100° C. to about 150° C., and said pressure is substantially atmospheric.

11. The process of claim 10 wherein said amine reactant is said polysubstituted piperazin-2-one, and comprising, recycling from none to all of said stripped, excess amine reactant as a first portion which is returned to said solventless reaction zone.

12. The process of claim 10 comprising, recycling none of said stripped, excess amine reactant; flowing all of said amine reactant to a second stripping zone; removing essentially pure excess amine reactant overhead; and, recycling said essentially pure excess amine to said solventless reaction zone.

13. The process of claim 11 including, recycling a minor portion of said stripped, excess amine reactant to said reaction zone, and flowing a major portion as a second portion, to a second stripping zone, removing essentially pure excess amine reactant overhead, and recycling said essentially pure excess amine to said solventless reaction zone.

14. The process of claim 13, comprising, in addition, removing a third portion of said stripped, excess amine reactant, diluting it with enough water at a temperature sufficient to reach the cloud point, and precipitating additional tri-substituted triazine product having a purity of at least 97%.

15. The process of claim 11 comprising, in addition, removing a third portion of said stripped, excess amine reactant, diluting it with enough water at a temperature sufficient to reach the cloud point, and precipitating additional tri-substituted triazine product having a purity of at least 97%.

* * * * *